United States Patent
Liu et al.

(10) Patent No.: US 7,419,635 B2
(45) Date of Patent: *Sep. 2, 2008

(54) PD/V$_2$O$_5$ DEVICE FOR COLORIMETRIC H$_2$ DETECTION

(75) Inventors: Ping Liu, San Diego, CA (US); C. Edwin Tracy, Golden, CO (US); J. Roland Pitts, Lakewood, CO (US); R. Davis Smith, II, Golden, CO (US); Se-Hee Lee, Lakewood, CO (US)

(73) Assignee: Midwest Research Institute, Kansas City, MO (US)

( * ) Notice: Subject to any disclaimer, the term of this patent is extended or adjusted under 35 U.S.C. 154(b) by 664 days.

This patent is subject to a terminal disclaimer.

(21) Appl. No.: 10/239,977

(22) PCT Filed: May 5, 2001

(86) PCT No.: PCT/US01/14411

§ 371 (c)(1),
(2), (4) Date: Jan. 29, 2003

(87) PCT Pub. No.: WO01/86266

PCT Pub. Date: Nov. 15, 2001

(65) Prior Publication Data

US 2004/0037740 A1    Feb. 26, 2004

Related U.S. Application Data

(60) Provisional application No. 60/202,153, filed on May 5, 2000.

(51) Int. Cl.
*G01N 33/00* (2006.01)

(52) U.S. Cl. .......................... 422/88; 422/50; 422/55; 422/56; 422/57; 422/83

(58) Field of Classification Search ................. 422/50, 422/55, 56, 57, 83, 86, 87, 88
See application file for complete search history.

(56) References Cited

U.S. PATENT DOCUMENTS

| 4,661,320 A | 4/1987 | Ito et al. |
| 4,706,493 A | 11/1987 | Chang et al. |
| 5,864,994 A | 2/1999 | Graf et al. |
| 6,723,566 B2 * | 4/2004 | Lee et al. .................. 436/144 |
| 2004/0023595 A1 * | 2/2004 | Ping et al. .................. 451/6 |

OTHER PUBLICATIONS

Patent Abstracts of Japan, vol. 012, No. 136 (p. 694), Apr. 26, 1988 & JP 62 257047 A(Hochiki Corp.), Nov. 9, 1987, abstract.
Ping, et al, "Stable Pd/V205 Optical H2 Sensor", Journal of Electrochemical Society, H76-H80 (2002).

* cited by examiner

*Primary Examiner*—Sam P. Siefke
(74) *Attorney, Agent, or Firm*—Paul J. White

(57) ABSTRACT

A sensor structure for chemochromic optical detection of hydrogen gas over a wide response range, that exhibits stability during repeated coloring/bleaching cycles upon exposure and removal of hydrogen gas, comprising: a glass substrate (20); a vanadium oxide layer (21) coated on the glass substrate; and a palladium layer (22) coated on the vanadium oxide layer.

4 Claims, 2 Drawing Sheets

PD/V₂O₅ DEVICE FOR COLORIMETRIC H₂ DETECTION

This application claims priority from U.S. Provisional Application Ser. No. 60/202,153, filed May 5, 2000.

CONTRACTUAL ORIGIN OF INVENTION

The United States Government has rights in this invention under Contract No. DE-AC3699GO10337 between the United States Department of Energy and the National Renewable Energy Laboratory, a division of the Midwest Research Institute.

BACKGROUND ART

The invention relates to an ultra-stable vanadium oxide thin film structure for the detection of hydrogen gas. The hydrogen gas is dissociated on the Pd catalyst into H atoms, and the $V_2O_5$ layer on which the Pd is coated functions as a $H^+$ insertion host. The Pd layer is thus stabilized, which upon combination with hydrogen is chemochromically changed.

Hydrogen is a plentiful, clean, non-polluting fuel. Hydrogen is currently used in many industries, and the US demand for hydrogen is approximately 140 billion cubic feet per year and growing. However, hydrogen is explosive at 4% in air. Therefore, it is critical to measure, monitor and control hydrogen wherever it is used.

In the gas detection art where sensors and measurement instrumentation for hydrogen gases detect and/or measure hydrogen, typically there is required a portable sensing device, a kit (where hydrogen gas detection and/or measurement is required in existing equipment), and sensor heads installed at points where hydrogen leaks are possible, or where monitoring is necessary (i.e., in internal combustion engines which operate using hydrogen as a fuel).

The problems associated with current $H_2$ detection devices is that these devices do not exhibit stable cycling during repeated coloring/bleaching processes and are encumbered by a narrow response range for detecting $H_2$.

DESCRIPTION OF THE RELATED ART

At present, $H_2$ detection may be accomplished through the use of various and sundry devices, including thin film Pd oxide devices. However, several problems or drawbacks are associated with the use of these hydrogen detecting devices. These problems are: they do not exhibit stable cycling during repeated coloring/bleaching processes; and they are encumbered by a narrow response range for detecting hydrogen.

Inadequate cycling stability during repeated coloring/bleaching processes and the narrow response range for detection of hydrogen gas, in the case of the Pd thin film is due to the fact that, in the presence of high concentrations of $H_2$, palladium hydride is formed and the sensor is destroyed.

DISCLOSURE OF THE INVENTION

One object of the present invention is to provide an ultra-stable palladium vanadium oxide film structure for chemochromic detection of hydrogen.

Another object of the present invention is to provide an ultra-stable palladium vanadium oxide structure for chemochromic detection of hydrogen that exhibits stable cycling during repeated coloring/bleaching processes.

A further object of the present invention is to provide an ultra-stable vanadium oxide film structure for chemochromic detection of hydrogen in which the proton insertion material contributes to stabilize the palladium layer, and exhibits a wider response range for detecting $H_2$.

In general, the invention is accomplished by providing a palladium/vanadium oxide layer sensor device in which, a $V_2O_5$ thin film is coated on a transparent or glass substrate. Thereafter, a palladium layer is evaporated onto the $V_2O_5$ thin film. The palladium layer serves as a catalyst material that facilitates reaction with hydrogen gas. That is, the hydrogen gas is dissociated on the Pd catalyst into H atoms, which diffuse into the $V_2O_5$ film The vanadium oxide layer acts as a hydrogen insertion host while the palladium layer is responsible for optical modulation. The presence of an ion storage host is vital to the stability of the palladium layer, and the sensor formed therefrom exhibits a wide response range for detecting hydrogen and shows very stable cycling during repeated coloring/bleaching processes.

DESCRIPTION OF THE INVENTION

Due to the fact that Pd/$WO_3$ sensors are saturated in the presence of just 2% $H_2$, and the fact that Pd sensors in the presence of $H_2$ form palladium hydride that results in destruction of the sensor, there is a need in the interest of safety to provide a $H_2$ sensor that still signals a chemochromic response to $H_2$ over a wide response range and in excess of 2%.

A further need exists in the art of chemochromic detection of hydrogen for a sensor that exhibits stable chemochromic cycling during repeated coloring/bleaching processes upon exposure and removal of $H_2$.

The Pd/$V_2O_5$ chemochromic hydrogen sensor is capable of providing a response above the narrow range of 2% hydrogen because, unlike $WO_3$, the Pd/$V_2O_5$ is not saturated at 2% $H_2$ or higher.

While not wishing to be bound by any theory as to why the Pd/$V_2O_5$ sensor is capable of functioning beyond the $H_2$ saturation point compared to a Pd/$WO_3$ sensor, it is nevertheless believed that, the Pd/$V_2O_5$ sensor structure does not change the thermodynamics of the system, i.e., if fully equilibrated, the Pd still forms a hydride; however, when a kinetically steady state is achieved, the sensor still has the capacity to detect high concentrations of hydrogen even in a higher than normal atmospheric pressurized hydrogen atmosphere.

Figure 1A:
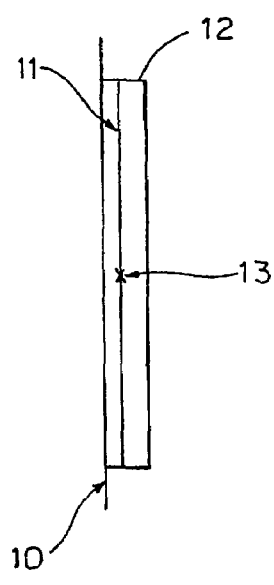
FIG. 1A shows a hydrogen sensor comprising $SiO_2$ deposited on a glass substrate, with Pd in turn deposited on the $SiO_2$ layer in which the interface between the $SiO_2$/Pd layer blocks the $H_2$.

Reference is now made to FIG. 1A in which there is shown a sensor comprising a glass substrate 10 on which is coated $SiO_2$, 11. A Pd layer 12 is coated onto the $SiO_2$. In this sensor device, as is depicted by arrow 13 directed onto the interface designated by x between the $SiO_2$ and Pd layers, $H_2$ 13 is blocked at the interface, because $SiO_2$ cannot react with hydrogen. Pd hydride is formed that undergoes phase transition at hydrogen concentration higher than 4%, resulting in substantial volume change and failure of the sensor.

Figure 1B:
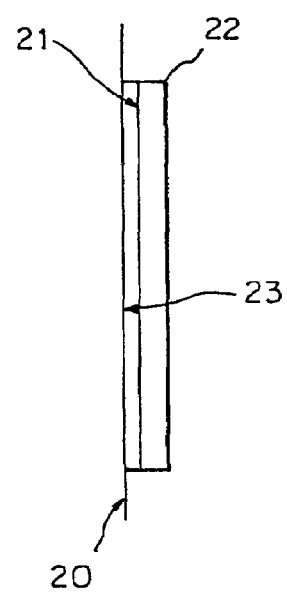
FIG. 1B shows a hydrogen sensor in which $V_2O_5$ is deposited on a glass substrate, with Pd in turn coated on the $V_2O_5$ layer in which the Pd/$V_2O_5$ interface does not block $H_2$.

On the other hand and by contrast, in FIG. 1B in which a glass substrate 20 is coated with a $V_2O_5$ layer 21, which in turn is coated by a Pd layer 22, $H_2$ 23 is not blocked at the interface between $V_2O_5$ and Pd. Accordingly, the vanadium oxide layer acts as a hydrogen insertion host in the $Pd/V_2O_5$ hydrogen sensor, while the palladium layer is responsible for the optical modulation.

The presence of an ion storage host is vital to the stability of the palladium layer, and, unlike the case, when $SiO_2$ is used in conjunction with a Pd layer, the Pd layer does not peel off and is not degraded in the presence of 2% $H_2$ (but actually starts forming hydride at room temperature in the presence of about 4% $H_2$).

The insertion of hydrogen in $V_2O_5$ is governed by the following equation:

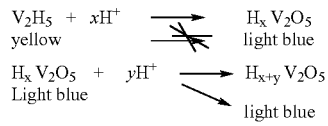

A control experiment was performed to show that the optical response was from the palladium layer.

The optical modulation is governed by the following equation:

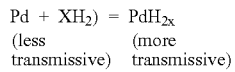

A hydrogen sensor of $Pd/V_2O_5$ was then prepared in which the $V_2O_5$=2014 Å and the Pd=31 Å.

A cathodic optical response of 2% transmittance change is observed, and this compels the conclusion that the Pd layer is contributing to the optical response of the sensor, but that the $V_2O_5$ layer acts as a non-coloring ion storage layer and operates to stabilize the entire chemochromic hydrogen detector structure.

Figure 2:
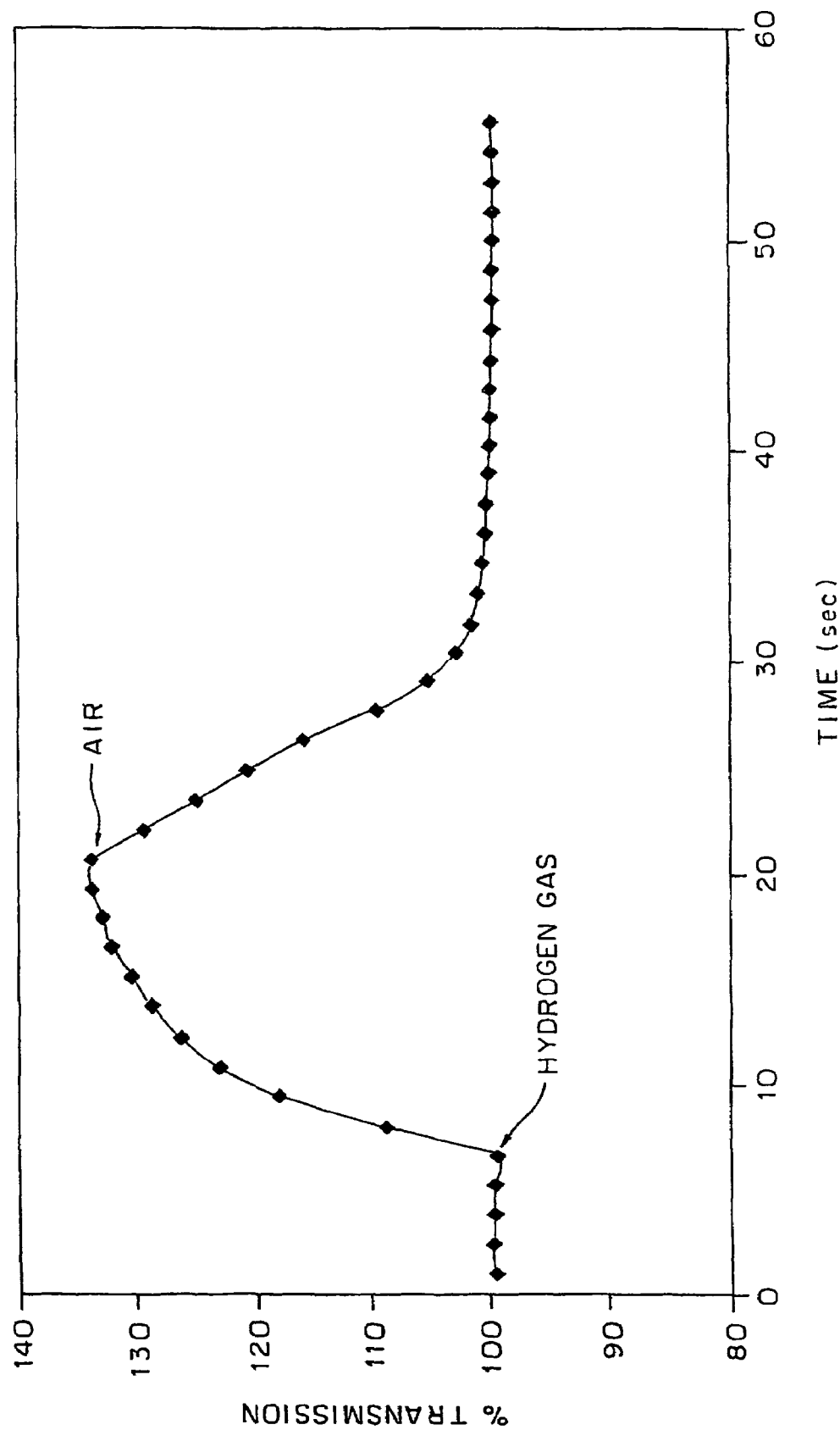
FIG. 2 is a graph showing percent relative transmission versus time for a 20 nm $VO_x$/30 nmPd sensor in the presence of 4% hydrogen.

FIG. 2 is a graph depicting percent relative transmission versus time for a 20 nm $VO_x$/30 nm Pd hydrogen sensor when exposed to a 4% hydrogen environment, and subsequently exposed to air.

Figure 3:
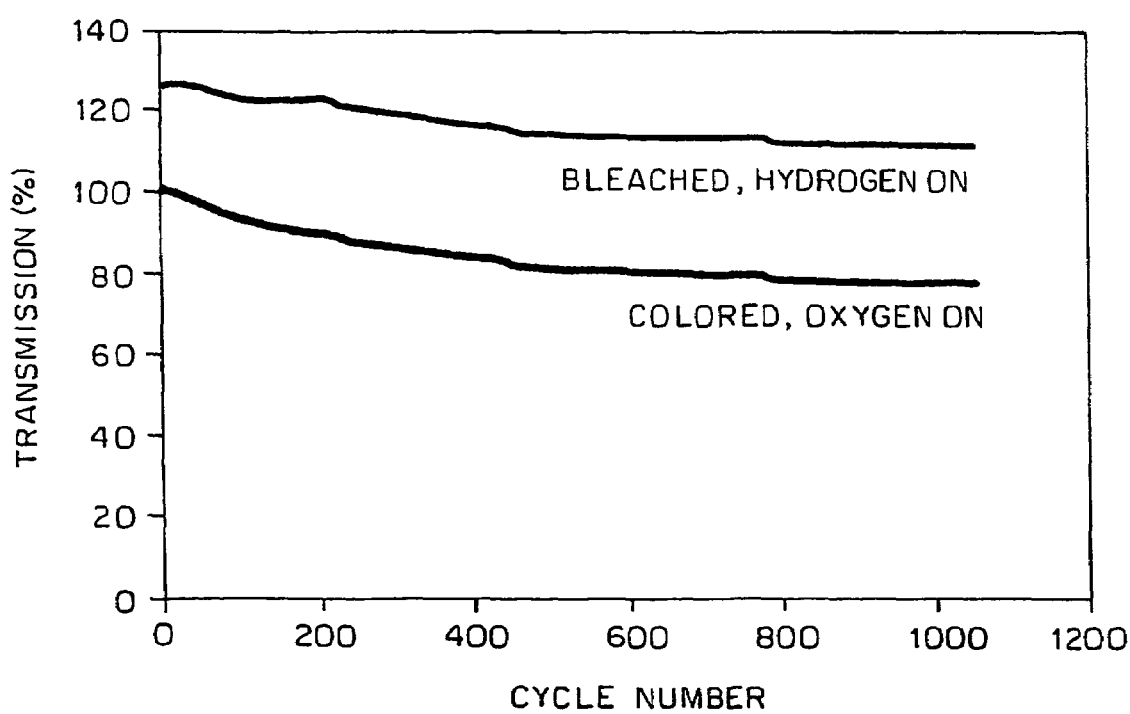
FIG. 3 is a graph showing percent relative transmission versus cycle number as a measure of cycling stability for a 20 nm $VO_x$/30 nmPd sensor in an environment of 4% $H_2$.

The cycling stability of a 20 nm $VO_x$/30 nm Pd hydrogen sensor at 4% hydrogen is shown in the graph of transmission relative percent versus cycle number in FIG. 3, where excellent cycling stability is exhibited during repeated coloring/bleaching cycles. The difference of transmittance between bleached and colored curves does not decrease with cycling.

From the foregoing, it is apparent that ion insertion host capability of the vanadium oxide layer is necessary to obtain stable cycling, and that, in the absence of an ion insertion host (as in the case of $SiO_2$) control experiment stable chemochromic cycling is not obtained due to the fact that palladium hydride is formed and the sensor is destroyed.

The $Pd/V_2O_5$ hydrogen sensor results show that: a proton insertion material is vital to stabilizing the palladium layer, although it does not contribute to the optical response; that the $Pd/V_2O_5$ hydrogen sensor is easy to make via thermal evaporation processes; and that a wide response range of between 1 to 100% $H_2$ concentration is available for detecting hydrogen.

The invention claimed is:

1. A sensor for detection of hydrogen gas over a wide response range, that exhibits stability in excess of 2% $H_2$ during repeated coloring/bleaching cycles upon exposure and removal of hydrogen gas, comprising:
   a substrate;
   a $V_2O_5$ layer coated on said substrate; and
   a 30 nm Pd layer coated on said $V_2O_5$ layer; wherein said $V_2O_5$ layer is a $H_2$ insertion host in the $Pd/V_2O_5$ hydrogen sensor, and said Pd layer is an optical modulator.

2. The sensor structure of claim 1 wherein the formed Vox/Pd sensor is characterized by a dimension of 20 nm for the $V_2O_5$ layer.

3. The sensor structure of claim 1 wherein the substrate is transparent.

4. The sensor structure of claim 1 wherein the substrate is glass.

* * * * *